(12) United States Patent
Khurana

(10) Patent No.: US 12,179,064 B2
(45) Date of Patent: Dec. 31, 2024

(54) SYSTEM, APPARATUS AND METHOD FOR TRAINING A SUBJECT

(71) Applicant: Vikas Khurana, Broomall, PA (US)

(72) Inventor: Vikas Khurana, Broomall, PA (US)

(*) Notice: Subject to any disclaimer, the term of this patent is extended or adjusted under 35 U.S.C. 154(b) by 148 days.

(21) Appl. No.: 17/717,284

(22) Filed: Apr. 11, 2022

(65) Prior Publication Data

US 2022/0323826 A1    Oct. 13, 2022

Related U.S. Application Data

(60) Provisional application No. 63/201,076, filed on Apr. 11, 2021.

(51) Int. Cl.
*A63B 24/00* (2006.01)
*A61B 5/00* (2006.01)
(Continued)

(52) U.S. Cl.
CPC ............ *A63B 24/0087* (2013.01); *A61B 5/42* (2013.01); *A61B 5/6891* (2013.01); *A61H 9/0078* (2013.01); *A63B 24/0006* (2013.01); *A63B 24/0062* (2013.01); *A63B 71/0054* (2013.01); *A63B 71/0622* (2013.01); *G01N 33/50* (2013.01); *G16H 40/67* (2018.01); *G16H 50/20* (2018.01); *A61H 2201/1246* (2013.01); *A61H 2201/1409* (2013.01); *A61H 2201/164* (2013.01); *A61H 2201/165* (2013.01); *A61H 2201/5007* (2013.01); *A61H 2201/5053* (2013.01); *A61H 2201/5056* (2013.01); *A61H 2201/5074* (2013.01);
(Continued)

(58) Field of Classification Search
CPC ............ A63B 24/0087; A63B 24/0006; A63B 24/0062; A63B 71/0054; A63B 71/0622; A63B 2024/0009; A63B 2024/0093; A63B 2024/0096; A63B 2071/0072; A63B 2220/836; A63B 2225/02; A63B 2230/045; A63B 2230/105; A63B 2230/305; A63B 2230/425; G16H 40/63; G16H 50/20; G16H 20/30; G16H 40/67; G16H 50/30; Y02A 50/30
See application file for complete search history.

(56) References Cited

U.S. PATENT DOCUMENTS 5,577,981 A * 11/1996 Jarvik .................... A63B 24/00
                                                            482/4
5,690,582 A * 11/1997 Ulrich ..................... A63B 22/02
                                                            482/52

(Continued)

*Primary Examiner* — Garrett K Atkinson
(74) *Attorney, Agent, or Firm* — Nitin Kaushik (57) ABSTRACT

A system (100) for training a subject such that the subject includes an input unit (102) having a number of sensors (112) that are configured to detect a number of physiological parameters of a user. A processing unit (104) is configured to receive the number of physiological parameters for comparing the number of physiological parameters with a set of predefined physiological parameters to generate a baseline signal (116A). An output unit (106) is configured to generate an instruction signal (118A) upon receipt of the baseline signal (116A) and a regulating unit (108) that is configured to regulate a speed of a game associated with a gamification engine (110) and a speed of an exercising apparatus (200) upon receipt of the instruction signal (118A).

15 Claims, 4 Drawing Sheets

(51) Int. Cl.
     *A61H 9/00*     (2006.01)
     *A63B 71/00*    (2006.01)
     *A63B 71/06*    (2006.01)
     *G01N 33/50*    (2006.01)
     *G16H 40/67*    (2018.01)
     *G16H 50/20*    (2018.01)

(52) U.S. Cl.
     CPC ........... *A61H 2203/0468* (2013.01); *A61H 2205/106* (2013.01); *A61H 2209/00* (2013.01); *A61H 2230/045* (2013.01); *A61H 2230/255* (2013.01); *A63B 2024/0009* (2013.01); *A63B 2024/0093* (2013.01); *A63B 2024/0096* (2013.01); *A63B 2071/0072* (2013.01); *A63B 2220/836* (2013.01); *A63B 2225/02* (2013.01); *A63B 2230/045* (2013.01); *A63B 2230/105* (2013.01); *A63B 2230/305* (2013.01); *A63B 2230/425* (2013.01); *G01N 2333/92* (2013.01); *G01N 2333/926* (2013.01); *G01N 2800/52* (2013.01)

(56) References Cited

U.S. PATENT DOCUMENTS

| | | | | |
|---|---|---|---|---|
| 5,846,086 | A * | 12/1998 | Bizzi | A63B 71/0622 482/902 |
| 7,018,211 | B1 * | 3/2006 | Birkholzer | A63B 69/00 434/257 |
| 7,494,450 | B2 | 2/2009 | Solomon | A63B 23/1209 482/69 |
| 7,625,316 | B1 * | 12/2009 | Amsbury | A63B 24/0062 482/8 |
| 7,780,450 | B2 * | 8/2010 | Tarry | G09B 19/0038 434/247 |
| 8,057,410 | B2 * | 11/2011 | Angold | A61H 3/008 601/5 |
| 8,328,691 | B2 * | 12/2012 | Lanfermann | A63B 69/00 482/901 |
| 9,015,638 | B2 * | 4/2015 | Kipman | G06F 3/0304 463/32 |
| 9,821,224 | B2 * | 11/2017 | Latta | A63F 13/213 |
| 10,445,930 | B1 * | 10/2019 | Saylor | G06T 7/80 |
| 10,646,153 | B1 * | 5/2020 | Berme | A61B 5/1036 |
| 10,758,780 | B2 * | 9/2020 | Putnam | G09B 19/003 |
| 10,828,551 | B2 * | 11/2020 | Putnam | G09B 19/0038 |
| 10,856,796 | B1 * | 12/2020 | Berme | G06F 3/013 |
| 2004/0087418 | A1 * | 5/2004 | Eldridge | A63B 69/0022 482/54 |
| 2006/0103627 | A1 * | 5/2006 | Watanabe | G03B 21/10 345/156 |
| 2010/0281432 | A1 * | 11/2010 | Geisner | G06F 3/011 715/849 |
| 2013/0145272 | A1 * | 6/2013 | Boggie | G06F 3/017 715/728 |
| 2013/0171600 | A1 * | 7/2013 | Yuasa | A61B 5/1036 434/258 |
| 2013/0171601 | A1 * | 7/2013 | Yuasa | G06V 40/23 434/258 |
| 2014/0141950 | A1 * | 5/2014 | Greiwe | A61H 1/005 482/146 |
| 2014/0276095 | A1 * | 9/2014 | Griggs | A61B 5/1128 600/595 |
| 2015/0099252 | A1 * | 4/2015 | Anderson | G06T 7/251 434/257 |
| 2015/0111698 | A1 * | 4/2015 | Abbondanza | G16H 40/67 482/4 |
| 2015/0196804 | A1 * | 7/2015 | Koduri | G06Q 10/0639 482/8 |
| 2016/0067548 | A1 * | 3/2016 | Shiao | A63B 21/0058 482/5 |
| 2016/0089573 | A1 * | 3/2016 | House | G16H 20/30 482/8 |
| 2016/0093081 | A1 * | 3/2016 | Kim | G06F 3/167 345/156 |
| 2016/0107309 | A1 * | 4/2016 | Walsh | A63B 21/0054 248/550 |
| 2016/0256740 | A1 * | 9/2016 | Rowe | G09B 19/0038 |
| 2016/0284132 | A1 * | 9/2016 | Kim | G06F 3/011 |
| 2017/0014684 | A1 * | 1/2017 | Burroughs | G16Z 99/00 |
| 2017/0076629 | A1 * | 3/2017 | Kim | G06V 40/23 |
| 2017/0100637 | A1 * | 4/2017 | Princen | G16H 20/30 |
| 2017/0246507 | A1 * | 8/2017 | Kennington | A63B 21/0087 |
| 2017/0282015 | A1 * | 10/2017 | Wicks | A63B 24/0075 |
| 2017/0312582 | A1 * | 11/2017 | Root, Jr. | A63B 24/0087 |
| 2018/0021616 | A1 * | 1/2018 | Orady | A63B 21/153 482/5 |
| 2018/0021627 | A1 * | 1/2018 | DeLuca | A63B 26/00 482/9 |
| 2018/0126248 | A1 * | 5/2018 | Dion | A63B 1/00 |
| 2018/0214729 | A1 * | 8/2018 | Rubin | A63B 24/0087 |
| 2019/0077007 | A1 * | 3/2019 | Mallinson | A61B 5/1118 |
| 2020/0009444 | A1 * | 1/2020 | Putnam | A61B 5/6891 |
| 2020/0014967 | A1 * | 1/2020 | Putnam | H04N 21/41265 |
| 2020/0068273 | A1 * | 2/2020 | Putnam | H04N 21/414 |
| 2020/0078640 | A1 * | 3/2020 | Putnam | A61B 5/743 |
| 2020/0192478 | A1 * | 6/2020 | Alcaide | G06F 3/015 |
| 2020/0401222 | A1 * | 12/2020 | Wisbey | H04R 5/033 |
| 2021/0046374 | A1 * | 2/2021 | Putnam | G09B 19/003 |
| 2021/0052967 | A1 * | 2/2021 | Putnam | H04L 65/613 |
| 2023/0329609 | A1 * | 10/2023 | Wisbey | G16H 20/70 |

* cited by examiner

SYSTEM, APPARATUS AND METHOD FOR TRAINING A SUBJECT

TECHNICAL FIELD

The present disclosure relates to a system, an apparatus and a method to train a subject. More particularly, the present disclosure relates to the system, apparatus and method for training the subject by monitoring health of the subject.

BACKGROUND

While a subject undergoing through intensive bodily regimes such as professional sports, exercises and/or physiotherapy then there are certain body movements that can be associated with the subject. For instance, an injured subject (patient) while undergoing physiotherapy courses, must know the accurate body movements to rectify the impaired body region.

Physiotherapies are crucial exercises/body movements that improves quality of life of the subject. In order to get a proper guidance for executing such body movements, a physiotherapist or any other medical personnel assist the patient/user to avoid any damaging movement regarding the impaired body region.

To realize the interaction of the physiotherapists or mimicking the assistance of physiotherapists, there are certain techniques known in the art that enables remote physiotherapy. Techniques like virtual reality and augmented reality are employed for delivering physiotherapies, exercises, or training, which ropes in minimal interaction of the physiotherapists while delivering such exercises remotely. Remote physiotherapy consumes less time in delivering the exercise guidance and enables the physiotherapists to cater to multiple subjects at a time or at different time frames.

One of the drawbacks associated with the remote physiotherapies incorporated with techniques such as virtual reality and augmented reality is the lack of instant real-time communication with the subject/patient to stop exercise or sports activity in case of any wrong body movement being carried out by the subject. Further, the remote physiotherapies may be proven dangerous for the subjects upon not getting notified for any inaccurate body movement. Due to damaging effects of such body movements, the affected body part of the patient/user may get permanently damaged, thus affecting the proper usage/employing of remote physiotherapies. Furthermore, there remains a significant risk of putting patients in an augmented reality or virtual reality game due to lack of communication with the subject/patient. For instance, this lack of communication with the patient may lead to dislodgment of the blood line during movement of the hand of the patient/user while performing dialysis on the patient. The physical presence of trained clinical professional not only watches for the damaging movements but also observes for subtle signs of clinical deterioration of the patient, these signs are generally not available during remote physiotherapies.

The available methodology of studying the pulse segment for multiple beats and then studying the heart rate variability requires at least 30 seconds of data before physiological change can be predicted, which limits instant communication with the user, during session of remote physiotherapy. In an example, while performing a dialysis procedure on the user, it requires an appropriate hand position of the user to circulate the blood from the hand of the user to the dialysis machine. Due to the lack of instant communication, the hand movement can lead to dislodgment of the blood line of the user and may lead to exsanguination and death of the user.

Thus, there is a need for a technical solution that overcomes the aforementioned problems of techniques involved in remote physiotherapy.

SUMMARY

In view of the foregoing, an aspect of the present disclosure provides a health monitoring system that includes one or more sensors of the input unit such that the one or more sensors are configured to detect one or more physiological parameters of a user. A processing unit communicatively coupled to the input unit, such that the processing unit receives the one or more physiological parameters sensed by the one or more sensors; and compares the one or more physiological parameters sensed by the one or more sensors with a set of predefined physiological parameters to generate a baseline signal. An output unit communicatively coupled to the processing unit, and configured to generate an instruction signal upon receipt of the baseline signal by the processing unit; and a regulating unit communicatively coupled to the output unit, and configured to regulate a speed of a game associated with a gamification engine and a speed of an exercising apparatus upon receipt of the instruction signal.

A recommendation engine is configured to provide real-time recommendations about an exercise performed by the user and an instruction engine is configured to generate the instruction signal upon receipt of the baseline signal.

The one or more sensors comprises a photoplethysmography (PPG) sensor, electro-cardiography (EKG) sensor, an electroencephalogram (EEG) sensor, an audio sensor, a gyroscopic sensor, or a motion sensor.

The one or more physiological parameters of the user comprises cardiovascular activity, heart rate variability, depth of breath, respirator rate, electroencephalogram, blood pressure, angulation of a joint, distance of a body part relative to an object, and distance of a body part relative to another body part of the user.

The gamification unit comprises a calibration switch that is configured to calibrate the game associated with the gamification unit based on a health condition of the user.

In another aspect, an apparatus for monitoring health of a user, the apparatus includes one or more sensors that are configured to detect one or more physiological parameters of the user. A processor communicatively coupled to the one or more sensors and configured to receive the one or more physiological parameters of the user to compare the one or more physiological parameters with a set of predefined physiological parameters to generate a baseline signal; and a gaming device communicatively coupled to the processor, and configured to generate an instruction signal upon receipt of the baseline signal such that the instruction signal is configured to regulate speed of a game associated with the gaming device.

The apparatus further comprises: a screen that is communicatively coupled to the processor and configured to provide real-time recommendations about an exercise performed by the user.

In another aspect, a method for monitoring physiological state of a user, the method includes the steps of: detecting one or more physiological parameters of the user by one or more sensors of an input unit; processing the one or more physiological parameters of the user by a processor of a processing unit such that the processor is adapted to compare the one or more physiological parameters with a set of predefined physiological parameters to generate a baseline signal; generating an instruction signal and providing real-time recommendations about an exercise to the user, upon receipt of the baseline signal by the output unit; and regulating a speed of a game associated with a gamification unit and a speed of an exercising apparatus.

BRIEF DESCRIPTION OF DRAWINGS

The above and still further features and advantages of embodiments of the present invention becomes apparent upon consideration of the following detailed description of embodiments thereof, especially when taken in conjunction with the accompanying drawings, and wherein.

To facilitate understanding, like reference numerals have been used, where possible, to designate like elements common to the figures.

DETAILED DESCRIPTION OF THE DRAWINGS

The various embodiments including the example embodiments are now described more fully with reference to the accompanying drawings, in which the various embodiments of the invention are shown. The invention may, however, be embodied in different forms and should not be construed as limited to the embodiments set forth herein. Rather, these embodiments are provided so that this disclosure is thorough and complete, and fully conveys the scope of the invention to those skilled in the art. In the drawings, the sizes of components may be exaggerated for clarity.

It is understood that when an element or component is referred to as being "on," "connected to," or "coupled to" another element or component, it can be directly on, connected to, or coupled to the other element or component or intervening elements or components that may be present. As used herein, the term "and/or" includes any and all combinations of one or more of the associated listed items.

Spatially relative terms, such as "top," "bottom," and the like, may be used herein for ease of description to describe one element or feature's relationship to another element(s) or feature(s) as illustrated in the figures. It is to be understood that the spatially relative terms are intended to encompass different orientations of the structure in use or operation in addition to the orientation depicted in the figures.

Embodiments described herein refer to plan views and/or cross-sectional views by way of ideal schematic views. Accordingly, the views may be modified depending on simplistic assembling or manufacturing technologies and/or tolerances. Therefore, example embodiments are not limited to those shown in the views but include modifications in configurations formed on basis of assembling process. Therefore, regions exemplified in the figures have schematic properties and shapes of regions shown in the figures exemplify specific shapes or regions of elements, and do not limit the various embodiments including the example embodiments.

The subject matter of example embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, the various embodiments including the example embodiments relate to the health monitoring system and methods.

As mentioned, there remains a need to provide a health monitoring system and method that enables quick or instant communication with a user to provide remote physiotherapy exercises to the user, therefore: the present disclosure provides a health monitoring system and method that enables a real-time communication with the user.

The terms "subject", "user" and "patient" are interchangeably used herein the context of the present disclosure.

The term "predefined physiological parameters" as used herein the context of the present disclosure are the parameters associated with a healthy subject, who is undergoing strenuous activity without any body/muscle straining. In other words, the term "predefined physiological parameters" are the ideal physiological parameters prescribed by a physiotherapists/doctor/medical-consultant that should be associated with the subject, while undergoing the strenuous activities. Further, the predefined physiological parameters may be the function of the health status of the user and therefore: the parameters may be different for different users/subjects/users.

The term "desired sympathetic and parasympathetic ratio/ratios" as used herein the context of the present disclosure refers to the ratios that are apt as per the clinical condition of the subject as determined by the physiotherapist and/or specialist. The sympathetic and parasympathetic ratio/ratios are plotted between low frequency (LF) and high frequency (HF) ratios (preferably in percentage). For example, for the subject attending conference (high mental stress) the LF to HF ratio is 81.2%, for the subject who is meditating the LF to HF ratio is 84.6%, for the subject undergoing through a surgery or any other painful activity the LF to HF ratio is 64.9%, i.e., when the ratio is recorded before or during the surgery, for the subject who is in mental stress (including various stressful events, for example work pressure) the LF to HF ratio is 81.7%, and for the subject who is in emergency condition the LF to HF ratio is 64.2%, i.e., when the ratio is recorded during or after the surgery.

The term "health status", "health condition" or "clinical condition" with reference to the user as used herein the context of the present disclosure refers to the general meaning of the health status of the user as known to the person skilled in the art.

The term "recommended posture" as used herein the context of the present disclosure refers to the ideal posture that should be attained by the user while performing an exercise.

The term "high frequency pulse sensing technology" as used herein the context of the present disclosure refers to pulse of a subject that is sampled at a high frequency (preferably up to 1000 Hz) to determine multiple physiological parameters such as heart rate variability and other pulse parameters to determine the physiological state of the subject.

The term "speed" and "resistance" with context to the exercising apparatus of the present disclosure are used interchangeably.

Figure 1:
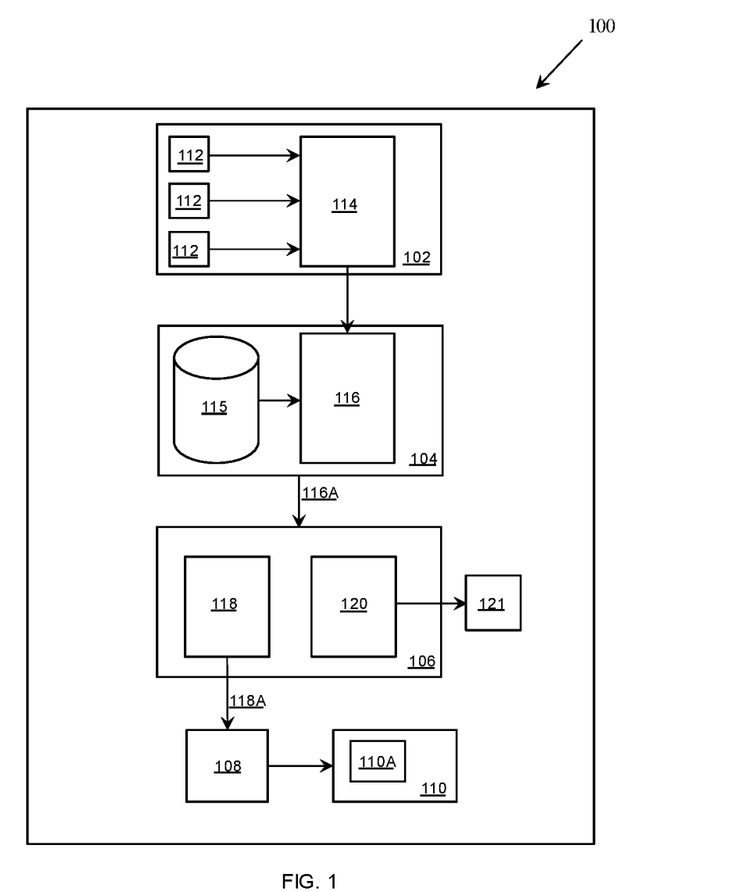
FIG. 1 illustrates a block-diagram of a health monitoring system, according to an embodiment herein.

FIG. 1 illustrates a system (100) for training a subject by monitoring physiological state of the user. The system (100)

includes an input unit (102), a processing unit (104), an output unit (106), a regulating unit (108), and a gamification unit (110).

The input unit (102) includes a number of sensors (referred to as "sensor" for single component) (112) and a transmitter (114). The processing unit (104) includes a processor (116) and a database (115).

The database (115) may be communicatively coupled to the processor (116) and may be adapted to store a set of predefined physiological parameters. The output unit (106) includes an instruction engine (118), a recommendation engine (120), and a display (121). The gamification unit (110) includes a calibration switch (122). The gamification unit (110) may be adapted to run a game.

The number of sensors (112) of the input unit (102) may be operatively coupled to a number of body parts of the user by a suitable means. The number of sensors (112) may be communicatively coupled to the transmitter (114) of the input unit (102). The transmitter (114) of the input unit (102) may be communicatively coupled to the processor (116) of the processing unit (104). The processor (116) may be communicatively coupled to the instruction engine (118) and the recommendation engine (120) of the output unit (106). The instruction engine (118) of the output unit (106) may be communicatively coupled to the regulating unit (108).

The recommendation engine (120) of the output unit (106) may be communicatively coupled to the display (121). The gamification unit (110) may be communicatively coupled to the regulating unit (108).

In operation, the system (100) may be adapted to monitor a physiological state of the user, while the user is undergoing any strenuous activity such as sports, exercise or physiotherapy. The number of sensors (112) of the input unit (102) may be adapted to detect/sense a number of physiological parameters of the user. The transmitter (114) may be adapted to transmit the number of physiological parameters of the user sensed by the number of sensors (112) to the processor (116) of the processing unit (104). The processor (116) may be adapted to receive the number of physiological parameters of the user and compare the number of physiological parameters sensed by the number of sensors (112) with the set of predefined physiological parameters stored in the database (115) of the processing unit (104). The processor (116) may be adapted to generate a baseline signal (116A) based on the comparison of the number of physiological parameters of the user with the set of predefined physiological parameters. The processor (116) may be adapted to transmit the baseline signal (116A) to the output unit (106). The instruction engine (118) of the output unit (106) may be adapted to generate an instruction signal (118A) upon receipt of the baseline signal (116A). The recommendation engine (120) may be adapted to provide real time recommendations to the user by way of the display (121), upon receipt of the baseline signal (116A). The display (121) may be adapted to suggest or showcase a recommended posture that may be fit for the user, while exercising. Further, the display (121) may be adapted to indicate the values of the forces exerted on the number of body parts of the user, while performing the exercise. The output unit (106) may be adapted to transmit the instruction signal (118A) to the regulating unit (108). The regulating unit (108) may be adapted to regulate a speed of the game associated with the gamification unit (110) based on the received instruction signal (118A).

As an example, for a healthy subject the maximum recommended heart rate (beats per minute) is 220 minus the age. For instance, a 30-year-old healthy subject, subtracting age (30) from 220 to get a maximum heart rate of 190 beats per minute. The maximum heart rate is adjusted for various clinical condition under the supervision of a health care provider. A patient with heart and kidney disease who is 30-year-old can have an adverse clinical outcome if his heart rate goes over 150 beats per minute.

In an embodiment, the gamification unit (110) may include a calibration switch (110A) to calibrate/alter the speed of the game based on the health status of the user or user's clinical condition, while performing the exercise. For instance, the user's clinical condition may include obstructive or restrictive lung disease.

In another embodiment, the regulating unit (108) may automatically bring the game associated with the gamification unit (110) to halt, upon receipt of the instruction signal (118A).

In another embodiment, the number of sensors (112) may be of type but not limited to photoplethysmography (PPG) sensor, electro-cardiography (EKG) sensor, and an electro-encephalogram (EEG) sensor.

In another embodiment, the system (100) may be configured to facilitate remote meditation for the user that is the system (100) may be adapted to alter the game based on the electrical activity sensed by the number of EEG sensors (112). The EEG sensor of the number of sensors (112) may be adapted to sense or record electrical signals corresponding to the brain activity of the user, while the user is meditating. The transmitter (114) may be adapted to transmit the electrical signals associated with the brain to the processor (116) of the processing unit (104). The processor (116) may be adapted to process the electrical signals of the brain of the user to generate the baseline signal (116A). The processor (116) may be adapted to transmit the baseline signal (116A) to the output unit (106). The instruction engine (118) of the output unit (106) may be adapted to generate the instruction signal (118A) upon receipt of the baseline signal (116A). The recommendation engine (120) may be adapted to provide real time recommendations to the user by way of the display (121), upon receipt of the baseline signal (116A). The display (121) may be adapted to suggest or showcase a recommended breathing patterns that may be fit for the user, while meditating. The output unit (106) may be adapted to provide a relaxing music to the user based on the instruction signal (118A), by way of an audio interface of the output unit (106). In another embodiment, the number of sensors (112) may be audio sensors that are adapted to sense sound associated with breathing of the user (hereinafter referred to as "breathing sound"). The regulating unit (108) may be adapted to regulate the speed of the game associated with the gamification unit (110) based on the breathing sound of the user. For example, if the user exhibits heavy breathing, then the output unit (106) may be adapted to slow down the speed of the game or stop the game associated with the gamification unit (110).

In another embodiment, the system (100) may be adapted to regulate the speed of the game associated with the gamification unit (110) based on the Borg rating (Borg scale), for example, for very hard exercise the Borg scoring is 17, for light exercise the Borg scoring is 11, for heavy hard exercise the Borg scoring is 15, and for very light exercise the Borg scoring is 9. The number of sensors (112) may be adapted to determine the Borg scoring based on the physiological parameters associated with the user such that the regulating unit (108) may be adapted to regulate the speed of the game based on Borg scoring.

In another embodiment, the system (100) may include a safety device that causes the regulating unit (108) to regulate the speed of the game associated with the gamification unit (110) even in the cases where the user may enjoy playing game while performing exercise irrespective of the physiological parameters of the user. The enjoyment in the game can trigger the user to undergo hard exercises even if the physiological parameters do not allow the user to perform such exercise. In such a scenario the safety device prevents the user to perform heavy exercises.

In another embodiment, the number of sensors (112) may be heart rate sensors that are configured to detect heart rate by video PPG of the patient or a calculated parameter thereof. In another embodiment, a high frequency pulse sensing technology may be used by the number of sensors (112) to detect/sense a number of physiological parameters of the user.

In another embodiment, a high frequency pulse sensing technology may be used by the number of sensors (112) to detect/sense a number of physiological parameters of the user or a calculated parameter thereof.

In another embodiment, the processor (116) may be adapted to evaluate a raw data (physiological parameters) detected by the number of sensors (112) and thereby performing an envelope wave analysis on a single pulse beat to provide an intra-beat variation that may lead to early detection of physiological deterioration in the physiological parameters of the user. Upon detection of the physiological deterioration of the physiological parameters, the processor (116) may be adapted to generate the baseline signal (116A) based on the deterioration of the physiological parameters. The baseline signal (116A) may be then transmitted to the instruction engine (118) for generating the instruction signal (118A). The instruction signal (118) thereby enables automatic adjustment of the game associated with the gamification unit (110).

In another embodiment, the gamification unit (110) may be adapted to run an augmented reality game or a virtual reality game.

In another embodiment, the number of physiological parameters of the user may include cardiovascular activity, and blood pressure of the user. The cardiovascular activity of the user includes photoplethysmography (PPG), electrocardiography (EKG), heart rate variability, and other such cardiac parameters.

In another embodiment, the system (100) may be adapted to regulate the speed of the game based on the combination of physiological parameters of the subject, for example, the regulating unit (108) may be adapted to regulate the speed of the game based on the combined data pertaining to heart rate and blood pressure of the user. Since, the heart rate and blood pressure both can vary during exercise, therefore: the regulating unit (108) may regulate the speed of the game considering variation in both the parameters i.e., variation in heart rate and variation in blood pressure. The physiological parameters may be considered individually or in combination, while the regulating unit (108) regulates the speed of the game associated with the gamification unit (110).

In another embodiment, the system (100) may be adapted to regulate the speed of the game based on static physiological parameters and dynamic physiological parameters associated with the user. The static physiological parameters may be the parameters that remains same before the exercise and after the exercise, for example age, weight, and resting stress levels, etc. The dynamic physiological parameters may be the parameters that show considerable change in their values after the exercise, for example, heart rate, blood pressure, pulse, stress, and mental activity etc.

In an exemplary embodiment, the number of sensors (112) may be deployed on the hand of the user, while performing a dialysis procedure on the user. While performing the dialysis procedure, there may be a requirement of taking blood from a particular hand, which requires an appropriate position of the hand. While performing the dialysis procedure, the user may undergo the exercising activity, which may require body movement of the user. The number of sensors (112) may be a movement sensor, or a gyroscopic sensor, that may be adapted to detect movement of the hand that is involved in the dialysis procedure. The transmitter (114) may be adapted to transmit the signals associated with the hand movement of the user to the processor (116) of the processing unit (104). The processor (116) may be adapted to process the signals related to hand-movement of the user to generate the baseline signal (116A). The processor (116) may be adapted to transmit the baseline signal (116A) to the output unit (106). The instruction engine (118) of the output unit (106) may be adapted to generate the instruction signal (118A) upon receipt of the baseline signal (116A). The output unit (106) may be adapted to transmit the instruction signal (118A) to the regulating unit (108). The regulating unit (108) may be adapted to regulate the speed of the game or to stop the game associated with the gamification unit (110) based on the instruction signal (118A). This regulation of the game speed facilitate protection for the user that prevents any dislodgement of the blood-access of the hand that is involved in the dialysis procedure.

Figure 2:
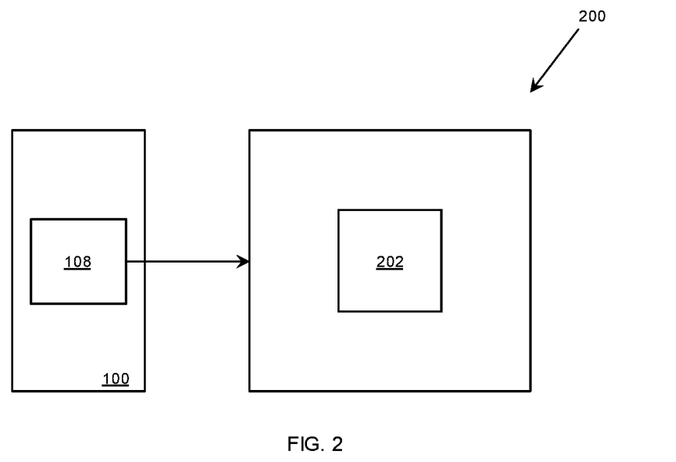
FIG. 2 illustrates an exercising apparatus, according to an embodiment herein.

FIG. 2 illustrates an exercising apparatus (200) that enables the user to perform an exercise. The exercising apparatus (200) includes a moving arrangement (202). While performing the exercise, the user needs to exert force on the moving arrangement (202) that sets the exercising apparatus (200) at a certain speed.

In operation, the system (100) monitors the physiological state of the user, while the user is performing the exercise on the exercising apparatus (200). Based upon the instruction signal (118A) generated by the instruction engine (118), the regulating unit (108) may be adapted to regulate the speed of the exercising apparatus (200) and thereby controlling the rate of exercise being performed by the user. The speed or resistance of the exercising apparatus may be, therefore: regulated as per desired sympathetic and parasympathetic ratios associated with the user. The resistance of the exercising apparatus may be, therefore: regulated as per the desired cardiovascular parameter for the user as set by the clinical provider. The adjustments can be based on the known condition of the patient based on the age, medical condition, disease state and baseline physiological stress. The adjustments can be based on the dynamic physiological stress experienced by the patient and detected by the sensors as he/she undergoes a particular exercise. In another exemplary embodiment, a pulmonary physiotherapy may be performed on the subject by deploying the number of sensors (112) on the chest of the user. The number of sensors (112) may be deployed on the chest of the user by means of a vest worn by the user and are adapted to detect respiratory rate, and a pulse rate of the subject. The number of sensors (112) may include but not limited to a high frequency pulse sensor, audio sensor and a movement sensor. The system (100), therefore: encourages the user to continue to perform pulmonary physiotherapy and provide feedback to reach the limit of instalments.

In another embodiment, the number of sensors (112) of the system (100) may be a regular pulse sensor such that the regular pulse sensors are configured to determine saturation of oxygen in the blood of the subject, heart rate of the subject, and hypoxia related condition of the subject.

In another embodiment, the number of sensors (112) may be adapted to detect chest expansion of the user, while the user may perform deep breathing exercises. The detection of chest expansion of the user may indicate breathing rate. The system (100) may be adapted to alter/regulate the game based on the measurement of the chest expansion of the user and thus encourage the user to continue to take deeper breaths for enhancing a pulmonary function of the user. The system (100) may be adapted to alter the game based on the user's clinical condition and thereby select and automate an appropriate physiotherapy treatment for the user. Upon selection of the appropriate physiotherapy treatment, the exercise may be tailored as per the clinical condition of the user. Thus, the system (100) encourages the user to achieve his/her maximum exercise potential in a gamification environment, while considering the clinical conditions of the user.

In another embodiment, a number of fencing sensors (not shown) may be deployed in the gamification environment that may appear like a virtual wall in the game. The virtual wall may be adapted to define a boundary of the gamification environment to the user and thereby preventing the user from hitting the wall, while performing the exercise.

In another embodiment, the game associated with the gamification unit (110) may be adapted to sense an environment around the game and adding a number of features of the environment to the game to provide an interactive experience to the user.

In an embodiment, the cardiac activity associated with the subject includes but not limited to photoplethysmography (PPG), electro-cardiography (EKG), heart rate variability.

Figure 3:
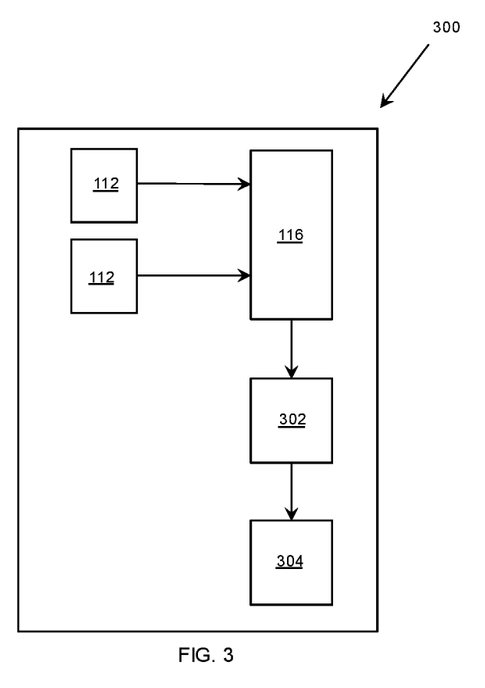
FIG. 3 illustrates an apparatus for monitoring health of the user, according to an embodiment herein.

FIG. 3 illustrates an apparatus (300) for training the subject. The apparatus (300) includes the number of sensors (112), the processor (116), a gaming device (302), and a screen (304).

The number of sensors (112) may be communicatively coupled to the processor (116). The processor (116) may be communicatively coupled to the gaming device (302) and to the screen (304).

In operation, the number of sensors (112) may be adapted to detect the number of physiological parameters of the user, while the user may be undergoing any strenuous activity. The processor (116) may be adapted to receive the number of physiological parameters of the user in order to generate the baseline signal (116A). The gaming device (302) may be adapted to generate the instruction signal (118A) upon receipt of the baseline signal (116A). The instruction signal (118A) may be adapted to regulate the speed of the game associated with the gaming device (302).

In an embodiment, the apparatus (300) further includes a screen (304) that may be communicatively coupled to the processor (116) of the apparatus (300). The screen (304) may be adapted to provide real-time recommendations about the exercise performed by the user.

In another embodiment, the number of sensors (112) may be deployed on a vest that may be worn by the user.

In another embodiment, the number of sensors (112) may be deployed on a hand-band that may be worn on a wrist of the user.

In another embodiment, the gaming device (302) may be a virtual reality headset. The virtual-reality head-set may be adapted to run a virtual-reality game.

In another embodiment, the gaming device (302) may be an augmented reality headset. The augmented-reality head-set may be adapted to run an augmented reality game.

In another embodiment, the processor (116) may be wirelessly coupled to the gaming device (302).

Figure 4:
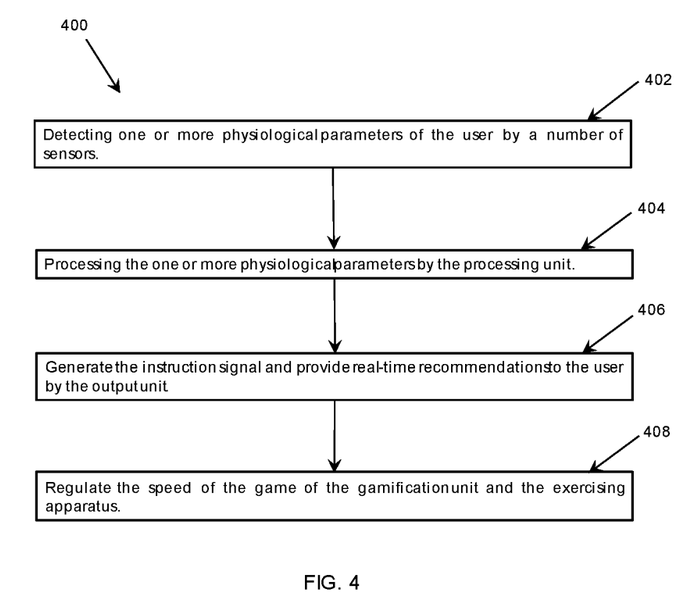
FIG. 4 illustrates a flow-chart showing a method for monitoring physiological state of the user.

FIG. 4 illustrates a flowchart depicting a method (400) for training the user. The method (400) involves following steps for monitoring the health of the user by way of the system (100).

At step (402), the system (100) may be adapted to detect a number of physiological parameters by the number of sensors (112) of the input unit (102) such that the number of sensors (112) may be operatively coupled to the number of body parts of the user. The transmitter (114) may be adapted to transmit the number of physiological parameters of the user sensed by the number of sensors (112) to the processor (116) of the processing unit (104).

At step (404), the system (100) may be adapted to process the number of physiological parameters by the processor (116) of the processing unit (104). The processor (116) may be adapted to receive the number of physiological parameters of the user and compare the number of physiological parameters sensed by the number of sensors (112) with the set of predefined physiological parameters stored in the database (115) of the processing unit (104). The processor (116) may be adapted to generate the baseline signal (116A) based on the comparison of the number of physiological parameters of the user with the set of predefined physiological parameters. The processor (116) may be adapted to transmit the baseline signal (116A) to the output unit (106).

At step (406), the system (100) may be adapted to generate the instruction signal (118A) by the instruction engine (118) and to recommend the user by the recommendation engine (120) of the output unit (106), upon receipt of the baseline signal (116A). The output unit (106) may be adapted to transmit the instruction signal (118A) to the regulating unit (108). The recommendation engine (120) may be adapted to provide real-time recommendations to the user by way of the display (121), upon receipt of the baseline signal (116A). The display (121) may be adapted to suggest or showcase a recommended posture that may be fit for the user, while exercising. Further, the display (121) may be adapted to indicate the values of the forces exerted on the number of body parts of the user, while performing the exercise.

At step (408), the system (100) may be adapted to regulate the speed of the game by the regulating unit (108). The regulating unit (108) may be adapted to receive the instruction signal (118A) to regulate the speed of the game associated with the gamification unit (110) and the speed of the exercising apparatus (200).

Certain advantages of the system (100) of the present disclosure are listed hereinbelow:—

- The system (100) may be adapted to provide quick or instant recommendations to the user about the exercise being performed by the user. The instant receipt of the recommendations allows the user to perform the exercise appropriately and thereby reducing the health damages, which could be caused due to continuation of the damaging exercise, for example if the user exercises in wrong posture, with wrong speed and with wrong intensity, then the system (100) is configured to provide quick or instant recommendations to the user about such actions caused due to wrong exercise. parameter (can be posture, speed, intensity etc).
- The high frequency pulse sensing technology used by the number of sensors (112) allow early prediction of fluctuation and physiological parameters like blood pressure, sympathetic to parasympathetic ratio, as compared to the heart rate variability.

The high frequency pulse sensing technology used by the number of sensors (112) allows quick prediction of deterioration of the physiological parameters and thereby allowing the user to take preventive measures timely to avoid any health damages.

The system (100) enables automatic adjustment of the game associated with the gamification unit (110), which provides precise, real-time and instantaneous feedbacks to the user.

The system (100) is capable for providing remote physiotherapy sessions by virtue of instant communications between the user and the system (100) by way of instant recommendations.

The system (100) is capable for providing multiple onsite supervised physiotherapy sessions by virtue of instant communications between the user and the system (100) by way of instant recommendations. This allows one physiotherapist to supervise multiple patients in a given instance.

The foregoing discussion of the present disclosure has been presented for purposes of illustration and description. It is not intended to limit the present invention to the form or forms disclosed herein. In the foregoing Detailed Description, for example, various features of the present invention are grouped together in one or more embodiments, configurations, or aspects for the purpose of streamlining the disclosure. The features of the embodiments, configurations, or aspects may be combined in alternate embodiments, configurations, or aspects other than those discussed above. This method of disclosure is not to be interpreted as reflecting an intention the present invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate embodiment of the present invention.

Moreover, though the description of the present disclosure has included description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

I claim:

1. A system for training a subject, wherein the system comprises:
   a. an input unit having one or more sensors configured to detect one or more physiological parameters of a user;
   b. a processing unit communicatively coupled to the input unit, such that the processing unit receives the one or more physiological parameters sensed by the one or more sensors and compares the one or more physiological parameters sensed by the one or more sensors with a set of predefined physiological parameters to generate a baseline signal;
   c. an output unit communicatively coupled to the processing unit, and is configured to generate an instruction signal upon receipt of the baseline signal by the processing unit; and
   d. a regulating unit communicatively coupled to the output unit, and is configured to regulate at least the speed of a game associated with a gamification engine of a gamification unit and a speed of an exercising apparatus upon receipt of the instruction signal, wherein the regulating unit is configured to regulate the speed of the game based on one or more:
      breathing sound of the user, wherein heavy breathing causes the regulating unit to slow down the game, or
      Borg rating (Borg scale) of the user's exertion level, wherein different Borg scores correspond to different exercise intensities, and the regulating unit adjusts the game speed accordingly, wherein the regulating unit is configured to regulate the speed of the exercising apparatus based on one or more:
      a combined data pertaining to heart rate and blood pressure of the user, considering variations in both parameters during exercise regulating the speed of the exercising apparatus, or
      static physiological parameters and dynamic physiological parameters associated with the user, allowing for adaptable speed regulation of the exercising apparatus based on changing physiological states.

2. The system of claim 1, the output unit comprising:
   a recommendation engine that is configured to provide real-time recommendations about an exercise performed by the user and an instruction engine that is configured to generate the instruction signal upon receipt of the baseline signal.

3. The system of claim 1, wherein the one or more sensors comprising a photoplethysmography (PPG) sensor, electrocardiography (EKG) sensor, an electroencephalogram (EEG) sensor, an audio sensor, a gyroscopic sensor, or a motion sensor.

4. The system of claim 1, wherein the one or more physiological parameters of the user comprising cardiovascular activity, heart rate variability, depth of breathing, respirator rate, stress, electroencephalogram (EEG) or blood pressure of the user.

5. The system of claim 1, wherein the gamification unit comprising a calibration switch that is configured to calibrate the game associated with the gamification unit based on a health condition of the user.

6. The system of claim 1, wherein the system further comprises
   a gaming device communicatively coupled to the processor, and configured to generate an instruction signal upon receipt of the baseline signal such that the instruction signal is configured to regulate speed of a game associated with the gaming device.

7. The system of claim 1, wherein the one or more sensors are configured to detect chest expansion of the user while the user performs breathing exercises, wherein detection of chest expansion of the user indicates breathing pattern.

8. The system of claim 1, wherein the regulating unit configured automatic adjustment of the speed of the game in real-time based on one of: changes in the baseline signal and measurement of chest expansion of the user.

9. The system of claim 1, further comprising altering the game based on the user clinical condition thereby selecting and automating an appropriate physiotherapy treatment for the user.

10. The system of claim 1, wherein the one or more sensors utilize high-frequency pulse sensing technology to predict early deterioration of the physiological parameters and enable the user to take timely preventive measures to avoid any health damage.

11. The system of claim 1, wherein the system enables remote physiotherapy sessions and multiple onsite supervised physiotherapy sessions through communications between the user and the system providing real-time recommendations.

12. A method for training a user, the method comprises:
   a. detecting one or more physiological parameters of the user by one or more sensors of an input unit;
   b. processing the one or more physiological parameters of the user by a processor of a processing unit such that the processor is adapted to compare the one or more physiological parameters with a set of predefined physiological parameters to generate a baseline signal;
   c. generating an instruction signal and providing real-time recommendations about an exercise to the user, upon receipt of the baseline signal by the output unit; and
   d. regulating at least a speed of a game with a regulating unit associated with a gamification unit and a speed of an exercising apparatus, upon receipt of the instruction signal, wherein the regulating unit is configured to regulate the speed of the game based on one or more:
   breathing sound of the user, wherein heavy breathing causes the regulating unit to slow down the game, or
   Borg rating (Borg scale) of the user's exertion level, wherein different Borg scores correspond to different exercise intensities, and the regulating unit adjusts the game speed accordingly,
   wherein the regulating unit is configured to regulate the speed of the exercising apparatus based on one or more:
   a combined data pertaining to heart rate and blood pressure of the user, considering variations in both parameters during exercise, or
   static physiological parameters and dynamic physiological parameters associated with the user, allowing for adaptable speed regulation based on changing physiological states.

13. The method of claim 12, wherein, the output unit comprises:
   providing real-time recommendations about an exercise performed by the user by a recommendation engine; and generating the instruction signal by an instruction engine upon receipt of the baseline signal.

14. The method of claim 12, wherein the one or more physiological parameters of the user comprising cardiovascular activity, heart rate variability, depth of breathing, respirator rate, electroencephalogram (EEG) or blood pressure of the user.

15. The method of claim 12, wherein the gamification unit comprising calibrating the game associated with the gamification unit based on a health condition of the user by a calibration switch.

\* \* \* \* \*